United States Patent
Glukhovsky et al.

(10) Patent No.: US 6,607,301 B1
(45) Date of Patent: Aug. 19, 2003

(54) DEVICE AND METHOD FOR DARK CURRENT NOISE TEMPERATURE SENSING IN AN IMAGING DEVICE

(75) Inventors: Arkady Glukhovsky, Nesher (IL); Gavriel Meron, Petach Tikva (IL); Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 09/806,714

(22) PCT Filed: Aug. 3, 2000

(86) PCT No.: PCT/IL00/00470
§ 371 (c)(1),
(2), (4) Date: Oct. 9, 2001

(87) PCT Pub. No.: WO01/10291
PCT Pub. Date: Feb. 15, 2001

(51) Int. Cl.[7] .............................. G01K 7/32; A61B 5/01; A61B 1/04
(52) U.S. Cl. ...................... 374/175; 374/117; 374/121; 374/141; 600/549; 600/109
(58) Field of Search ................. 374/175, 117, 374/141, 136, 121, 120, 128; 356/43, 44; 600/474, 549, 101, 109, 117, 118, 127, 153, 160, 562, 573, 104–106; 348/65, 74–77, 81–85, 909; 250/339.04, 352; 327/512

(56) References Cited

U.S. PATENT DOCUMENTS

| | | | | |
|---|---|---|---|---|
| 3,937,086 A | * | 2/1976 | von Thuna | .................. 374/175 |
| 3,971,362 A | | 7/1976 | Pope et al. | |
| 4,246,784 A | | 1/1981 | Bowen | |
| 4,278,077 A | | 7/1981 | Mizumoto | |
| 4,643,587 A | * | 2/1987 | Makabe et al. | .............. 374/124 |
| 4,646,723 A | * | 3/1987 | Arakawa | ..................... 600/109 |
| 4,646,724 A | * | 3/1987 | Sato et al. | ................... 600/109 |
| 4,689,621 A | | 8/1987 | Kleinberg | |
| 4,744,672 A | * | 5/1988 | Tursky et al. | ................ 374/178 |
| 4,844,076 A | | 7/1989 | Lesho et al. | |
| 4,891,970 A | * | 1/1990 | Remboski, Jr. | .............. 374/144 |
| 5,098,197 A | | 3/1992 | Shepard et al. | |
| 5,279,607 A | | 1/1994 | Schentag et al. | |
| 5,354,130 A | * | 10/1994 | Seppa et al. | .................. 374/175 |
| 5,508,740 A | * | 4/1996 | Miyaguchi et al. | .......... 348/244 |
| 5,604,531 A | * | 2/1997 | Iddan et al. | .................... 348/76 |
| 5,640,235 A | * | 6/1997 | Iwasaki | ........................ 356/218 |
| 5,746,511 A | | 5/1998 | Eryurek et al. | |
| 5,819,736 A | | 10/1998 | Avny et al. | |
| 5,833,603 A | | 11/1998 | Kovacs et al. | |
| 5,853,005 A | | 12/1998 | Scanlon | |
| 6,184,511 B1 | * | 2/2001 | Yamashita | ................ 250/201.2 |

FOREIGN PATENT DOCUMENTS

| | | |
|---|---|---|
| GB | 2 353 166 A * | 2/2001 |
| JP | 4109927 | 4/1992 |
| JP | 5015515 | 1/1993 |

OTHER PUBLICATIONS

Jones, B.K., "Electrical Noise Thermometer," Appl. Phys. vol. 16, No. 1, pp. 99–102 (May 1978).*
The Radio Pill, Rowlands, et al., British Communications and Electronics, Aug. 1960, pp. 598–601.
Video Camera to "TAKE"—RF System lab, no date.

(List continued on next page.)

Primary Examiner—Diego Gutierrez
Assistant Examiner—Stanley J. Pruchnic, Jr.
(74) Attorney, Agent, or Firm—Eitan, Pearl, Latzer & Cohen Zedek, LLP.

(57) ABSTRACT

A device, method and system for sensing the temperature of an environment. An image sensor may be introduced into an environment having an image sensing module. The dark current noise of the image sensor may be sensed, and the temperature of the image sensor (and environment) calculated. Such a device, system and method may be used in, for example, a medical imaging device.

37 Claims, 4 Drawing Sheets

OTHER PUBLICATIONS

Wellesley company sends body montiors into space—Crum, Apr. 1998.

Wireless transmission of a color television moving image from the stomach using a miniature CCD camera, light source and microwave transmitter. Swain CP, Gong F, Mills TN. Gastrointest Endosc 1997;45:AB40.

CCD arrays cameras and displays, Holst G.C. p128, $2^{nd}$ Edition, Spie Press 1998 (no month).

Photobit PB–159 DX Product Specification, Aug. 1998 (Version 3.0).

www.io.com—Random Electrical Noise: A Literature Survey, Research Comments from Ciphers, Ritters, 1999 (Dec).

* cited by examiner

DEVICE AND METHOD FOR DARK CURRENT NOISE TEMPERATURE SENSING IN AN IMAGING DEVICE

CROSS REFERENCE TO RELATED APPLICATIONS

This application claims the benefit of PCT patent application PCT/IL00/00470, filed Aug. 4, 2000, titled "A METHOD FOR TEMPERATURE SENSING", which was published in English, and which is incorporated herein by reference in its entirety. PCT/IL00/00470 claims the benefit of Israeli Patent Application 131242, filed Aug. 4, 1999, entitled "A METHOD FOR TEMPERATURE SENSING", which is incorporated herein by reference in its entirety.

FIELD OF THE INVENTION

The present invention relates to a method and system for measuring the temperature of an environment, such as the interior of the body.

BACKGROUND OF THE INVENTION

In many circumstances it is important to measure the temperature inside a material body. Such circumstances may occur during industrial processes or exploration and analysis processes, such as in geophysical probing or in medical diagnostics and treatment of internal parts of the body.

Conventional thermometry and absolute thermometry are known methods for measuring temperature.

Conventional thermometry is based upon the temperature coefficient of properties of materials, such as resistance or mechanical expansion.

Absolute thermometry is a method which directly measures thermal energy of a sensor resistance. This method is based upon the known physical phenomenon of spontaneous thermal noise arising from the Brownian motion of ionized molecules within a resistance.

Thermal noise, which can be discussed in terms of thermal current, provides a direct measurement of temperature on a thermodynamic scale, thus the Boltzmann constant defines the temperature. The phenomenon of thermal noise is derived, for example, in the book: CCD arrays cameras and displays by Hoist G. C., p. 128, $2^{nd}$ edition, SPIE Press, 1998. The formula used to define thermal current is:

$$<i_n^2>=kTC$$

where k is the Boltzmann constant, T is the temperature of a sensor, and C is the capacitance of the sensor. Thus the magnitude of the signals produced by the thermal current is directly proportional to the square root of the temperature of the sensor. Experiments have indicated that the signal doubles with the increase of 7° C. (degrees Centigrade), which means that a resolution better than 0.1° C. is achieved.

In image sensors, the thermal current produced in an operating photodetector device, when no optical radiation impinges on the detector, is called "dark current". In CCD cameras dark current is basically charge which accumulates in the CCD pixels due to thermal noise. The effect of dark current is to produce an additive quantity to the electron count in each pixel.

U.S. Pat. No. 3,937,086 to von Thuna, U.S. Pat. No. 5,354,130 to Seppa et al. and U.S. Pat. No. 5,098,197 to Shepard et al. all describe devices for measuring the absolute temperature of a body material by receiving and analyzing the thermal noise of the body material.

U.S. Pat. No. 4,246,784 to Bowen describes a method for noninvasive temperature measurement of the interior of a body using the acoustic thermal noise spectrum of the measured body.

None of these temperature measurement methods utilize an image sensor to measure the thermal noise of a body material.

SUMMARY OF THE INVENTION

The present invention provides a method and system for sensing the temperature of an environment, such as inside a body, by calculating the temperature of an image sensor in the environment and deducing the environment's temperature from the image sensor's calculated temperature. The temperature of the image sensor is calculated by measuring its generated dark current noise.

The method and system of the present invention have the advantage of utilizing an image sensor, in which thermal noise is easily detectable, for deducing the temperature of a material body. Furthermore, according to the invention, a single sensor is utilized for obtaining visual data and data relating to the temperature of the environment. Thus, diverse information about an environment can be obtained utilizing a single sensing device.

There is thus provided according to the present invention a method for sensing the temperature of an environment comprising the steps of introducing into an environment an image sensor having an image sensing module, sensing the dark current noise of the image sensor, calculating the temperature of the image sensor, calculating the temperature of the environment and optionally displaying the calculated environment temperature.

It will be appreciated that the term "environment" in the present invention relates to a space enclosed within walls in which it is desired to measure the temperature of the space and/or of the walls.

The temperature of the image sensor is indicative of the temperature of it's immediate surroundings and, relying on known factors such as heat distribution, distance from the image sensor, etc., the temperature of further areas can also be calculated.

The image sensors utilized in the invention can be digital cameras or video cameras such as vidiocon, CCD cameras or CMOS cameras.

The present invention further provides a system for sensing the temperature of an environment. The system comprises an image sensor having an image sensing module in communication with an integrating unit for detecting the dark current of the image sensor image sensing module and for calculating the temperature of the image sensor. The integrating unit may further calculate the temperature of the environment or the temperature of the environment may be calculated, based on data from the integrating unit, by a separate unit that is in communication with the integrating unit The integrating unit may have an amplifying function for amplifying signals received from the image sensor.

The communication between the image sensor and integrating unit can be optionally controlled according to the illumination conditions, optionally through a switch which enables communication only during periods in which the sensor is not illuminated.

BRIEF DESCRIPTION OF THE FIGURES

The present invention will be understood and appreciated more fully from the following detailed description taken in conjunction with the figures in which.

DETAILED DESCRIPTION OF THE INVENTION

Analytical and diagnostic processes which utilize image sensors to monitor environments could benefit from obtaining information relating to the temperature of the environment, as a local change of temperature can indicate an irregular event.

For example, U.S. Pat. No. 5,604,531, which is assigned to the common assignees of the present application, describes a swallowable capsule that can pass through the entire digestive tract and operate as an autonomous video endoscope U.S. Pat. No. 5,604,531, is hereby incorporated by reference. The swallowable capsule includes a) a camera system, b) an optical system for imaging an area of interest onto the camera system and c) a transmitter which transmits the video output of the camera system. Visual data obtained by the swallowable capsule can indicate, inter alia, the location of pathologies in the gastrointestinal tract. Also a local change of temperature in the gastrointestinal tract can be indicative of a pathology. Thus, the information obtained by visual means can be complemented and focused by information relating to local temperature in the gastrointestinal tract.

The method of the present invention enables contemporary visual monitoring and temperature sensing.

Figure 1:
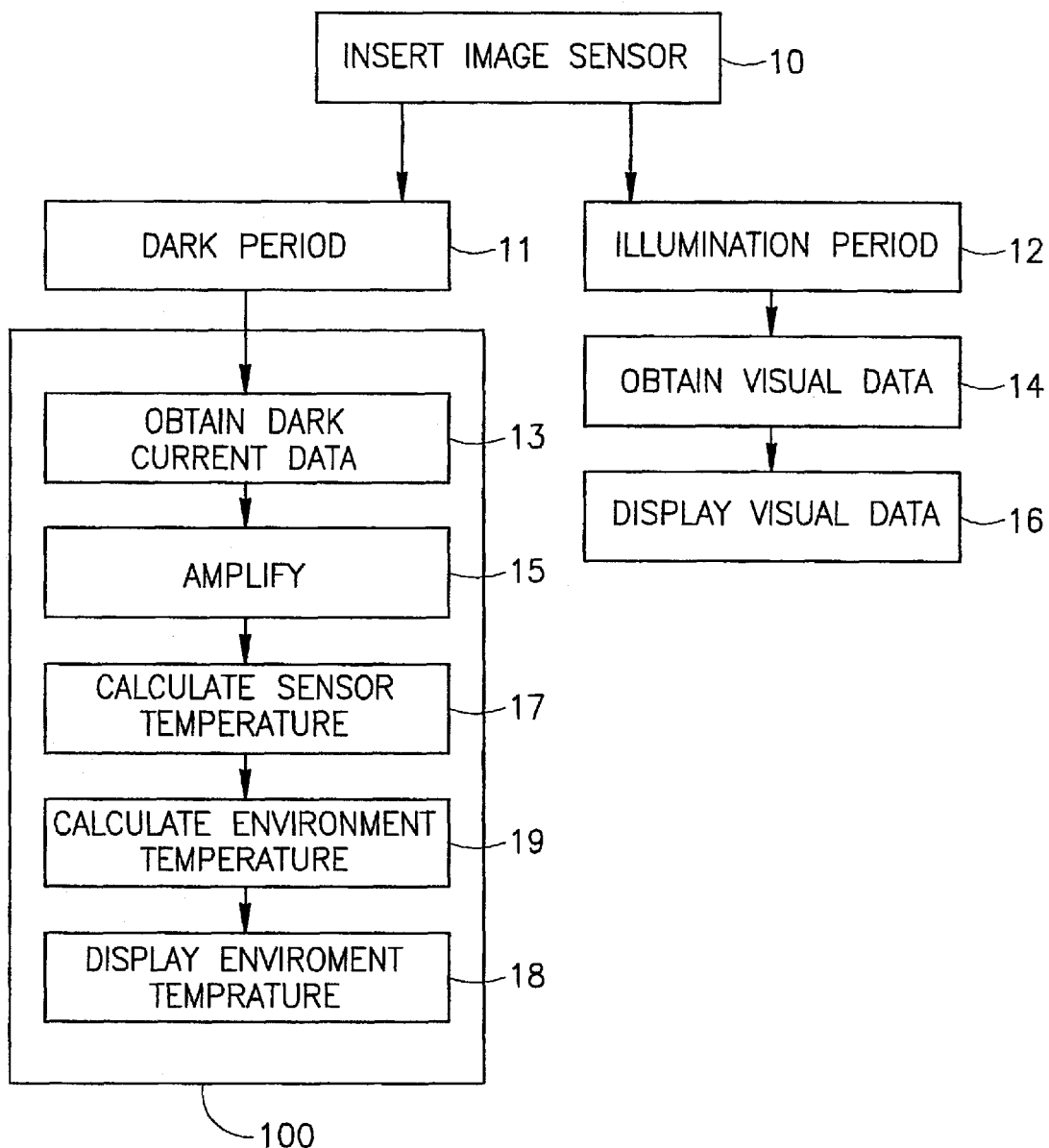
FIG. 1 is a block diagram representing an embodiment of the method according to the invention.

The method is schematically described by a block diagram shown in FIG. 1. An image sensor, such as in the above mentioned swallowable capsule, is inserted 10 into an environment, such as the gastrointestinal tract.

Illumination is provided intermittently, either by elements connected to the image sensor itself or by external sources. When illumination is provided 12 only visual data is obtained 14 and displayed 16. A process for obtaining and displaying visual data is described, for example, in the above mentioned U.S. Pat. No. 5,604,531.

In an intermittent dark period 11 an integrating unit 100 is activated to obtain dark current data 13 from the image sensor, though it is not imperative to shut off illumination in order to obtain data relating to dark current noise, as will be discussed in more detail below.

The integrating unit 100 is a processor capable of amplifying the obtained data 15, if necessary, and calculating the image sensor temperature 17 using the known equations derived for thermal noise. It will be appreciated that these equations are an approximation of a complex phenomenon and that calibration should be employed in order to deduce the actual calculations that will be applied.

The environment temperature is then calculated 19, either by the integrating unit 100 or by a separate unit in communication with the integrating unit 100. Calculations of the environment temperature are based on the existence of thermal equilibrium between the image sensor and environment. These calculations take into account energy dissipation from the image sensor. Local temperature or the average temperature within the environment may be calculated, depending on specific requirements. The calculated temperature may then be displayed 18.

It will be appreciated that the various calculations are carried out by software or software means executable on computing means such as a computer or similar data processors, microprocessors, embedded processors, microcomputers, microcontrollers etc., The integrating unit 100 may comprise separate processors, which need not all be physically connected. Some of the functions carried out by integrating unit 100, such as calculating the image sensor temperature 17 and calculating the environment temperature 19, can be carried out in processors that are external to the environment and that are fed with data from the integrating unit 100 by communication such as by IR or radio. Indeed, if an operator is to note the temperature of the environment, at least the function of displaying the calculated temperature 18 must be performed externally to the environment.

Integrating unit 100 may be in communication with other units to further process and use the data obtained by it. For example, a swallowable capsule, such as described in U.S. Pat. No. 5,604,531, may comprise a sample chamber for collecting samples from the environment of the digestive tract. The process of collecting a sample can be controlled by integrating unit 100, such that samples are collected only in locations along the digestive tract in which a predetermined temperature is prevalent.

Figure 2:
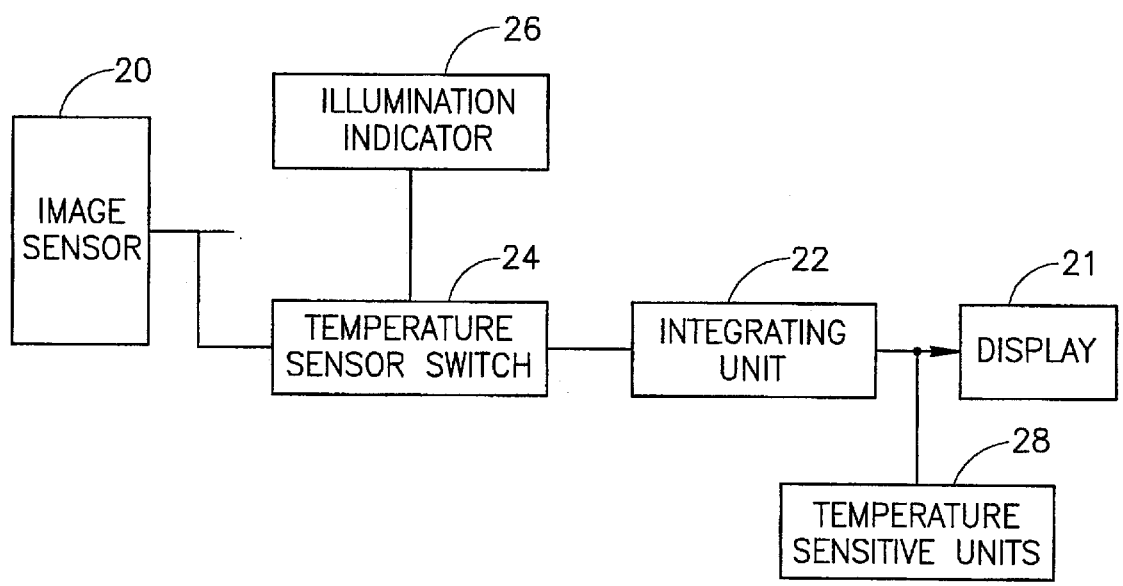
FIG. 2 is a schematic illustration of an embodiment of the system according to the invention.

Reference is now made to FIG. 2 which is a schematic illustration of the system according to an embodiment of the invention. The system comprises an image sensor 20 having an image sensing module which includes a pixel array (as demonstrated in FIG. 3) in communication with an integrating unit 22. Communication is enabled by temperature sense switch 24 which is controlled by illumination indicator 26, such that communication is enabled only during dark periods.

When communication between the image sensor 20 and integrating unit 22 is established, integrating unit 22 receives dark current data from image sensor 20.

As will be discussed below, it is possible to calculate the image sensor's 20 temperature based on dark current data obtained from a single pixel of the image sensor pixel array, though data obtained from a higher number of pixels will achieve more accurate results. It is therefore possible to keep a portion of the image sensor's 20 pixels of the pixel array, constantly unexposed to illumination, and obtain dark current data from the unexposed pixels, without having to shut off the illumination.

Thus, dark current data can be obtained also during constant illumination by either covering a portion of the pixels of the pixel array or by having a portion of the pixel array pixels outside of the image field, e.g. the pixels in the periphery of the pixel array.

The integrating unit 22 is a processor capable of amplifying the dark current signal and calculating the image sensor temperature from the dark current signal. It is further capable of calculating the environment temperature from the image sensor temperature and is capable of displaying the calculated environment temperature 21. Integrating unit 22 may control different temperature sensitive units 28, such as the sample chamber described above, in correspondence with predetermined temperatures.

Figure 3:
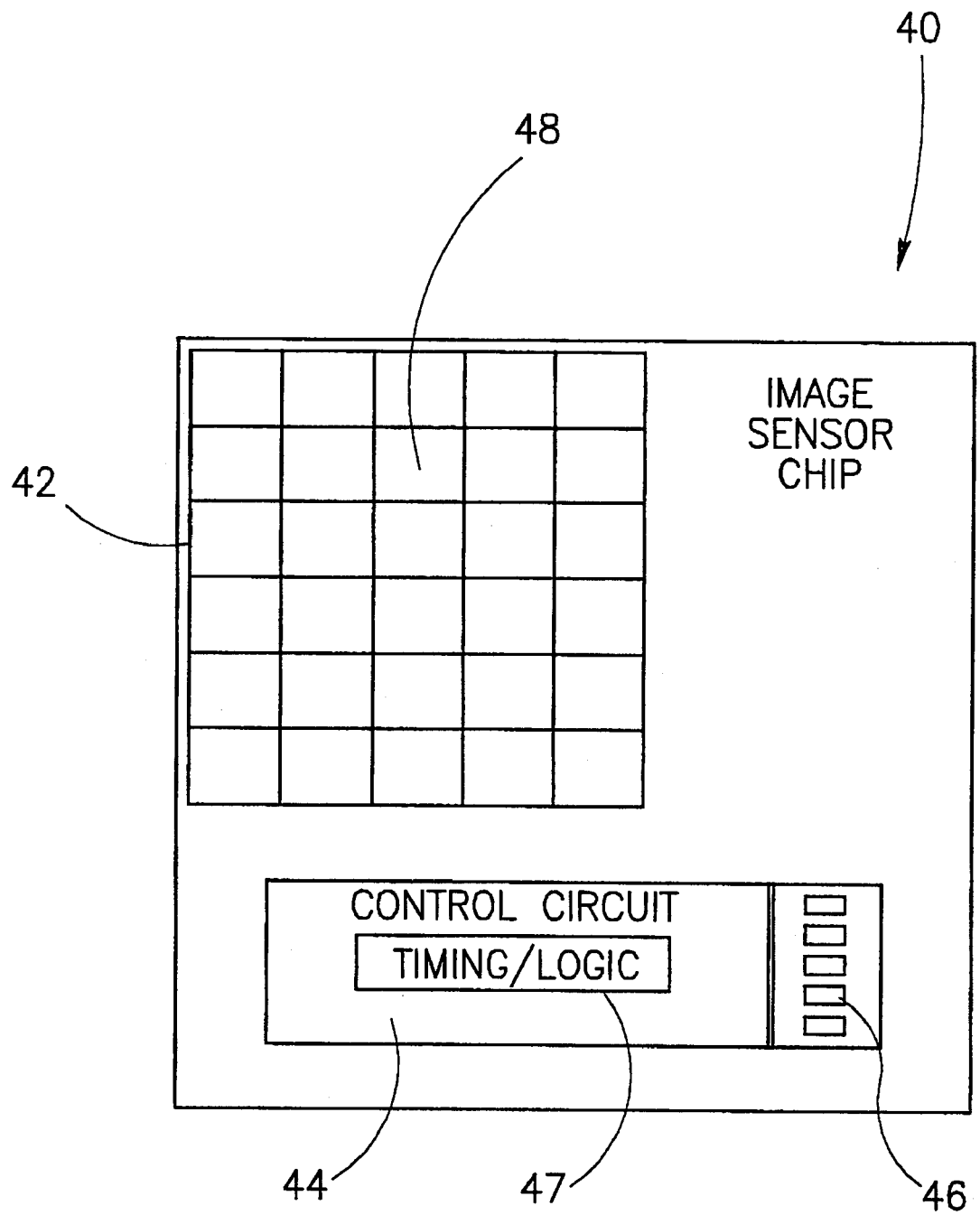
FIG. 3 is a schematic illustration of a functional block layout of the image sensor according to the invention.

Reference is now made to FIG. 3 which is a schematic illustration of a functional block layout of the image sensor according to the invention. The image sensor comprises a single chip 40 having an image sensing module 42 and a control circuits area 44. The image sensing module 42 includes a pixel array 48 for capturing an image. The control circuits area 44 includes the timing and logic circuitry 47 and A/D circuitry 46.

Signals can be received from all the pixels of the pixel array 48. Dark current is received from pixels that are not illuminated or from pixels during a dark period whereas current signals received from an illuminated pixel are the summation of the dark current and light current of the pixel. The accumulation of signals from all the pixels is converted to data which is communicated through a transmitter to the integrating unit for decoding and for displaying a visual representation and/or the temperature derived from the data.

Figure 4:
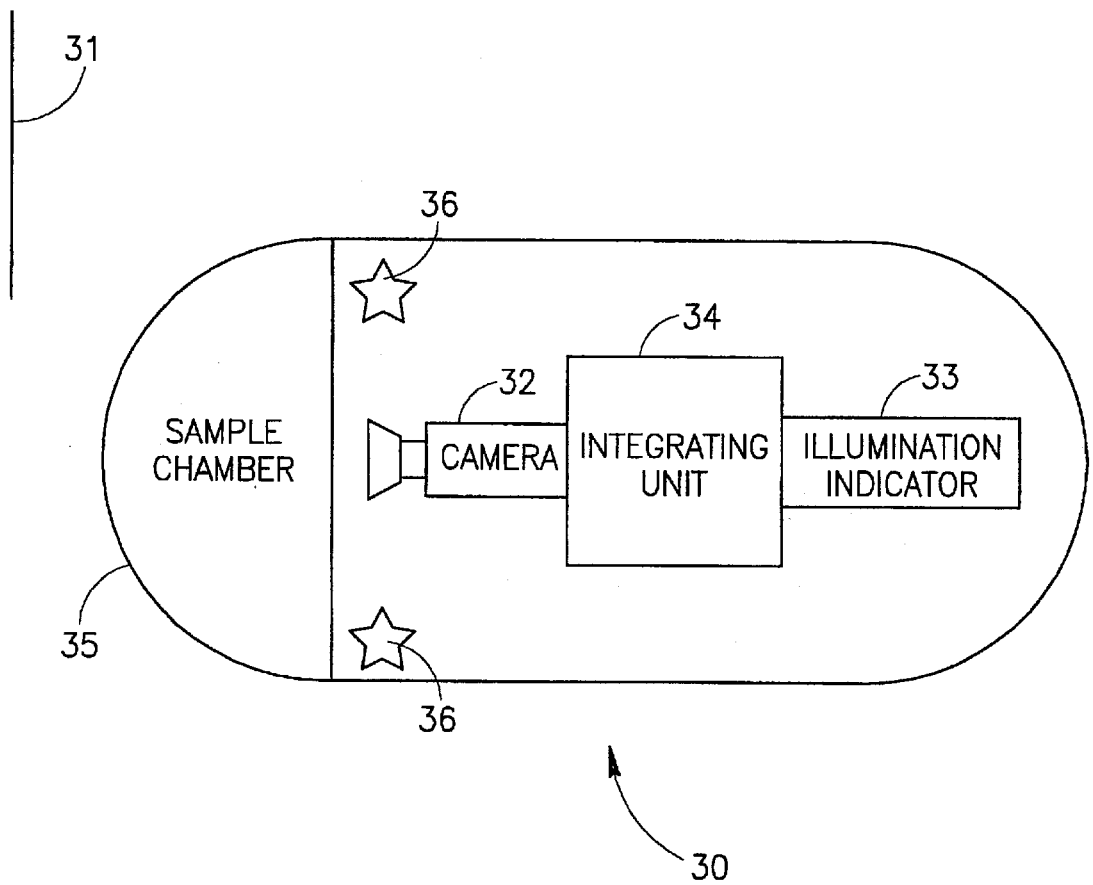
FIG. 4 is a schematic illustration of a medical device comprising the system according to the invention.

The system of the invention will be further described and demonstrated by FIG. 4 which is a schematic illustration of a medical device comprising a system according to the invention.

The medical device illustrated in FIG. 4 is a swallowable capsule, generally referenced 30, such as that described in the above mentioned U.S. Pat. No. 5,604,531. Swallowable capsule 30 comprises a CMOS camera 32, that is in communication with integrating unit 34. The swallowable capsule 30 further comprises illuminating elements 36 that are in communication with illumination indicator 33. The gastrointestinal tract walls 31 are illuminated by illuminating elements 36, in intermittent pulses, capturing consecutive images of the gastrointestinal tract walls 31 by camera 32, enabling an operator to view the gastrointestinal tract walls. Communication between camera 32 and integrating unit 34 is enabled in between illumination pulses when illumination indicator 33, sensing the lack of illumination, activates the temperature sense switch (not shown) to an ON position.

Alternatively, the illumination indicator 33 may be activated by the operator to simultaneously turn off the illumination elements 36 and switch the temperature sense switch to an ON position.

Once communication is established between camera 32 and integrating unit 34 dark current signals generated from camera 32 are received and processed, as described above, by integrating unit 34. The calculated gastrointestinal temperature is displayed on a display unit external to the gastrointestinal tract.

Swallowable capsule 30 further comprises a sample chamber 35 for collecting samples from the gastrointestinal tract environment. The collected sample may be cells from the gastrointestinal tract walls or a liquid sample from the gastrointestinal tract environment. The mechanism for collecting samples, which can be any suitable mechanism known in the art, is controlled by integrating unit 34, such that it is activated in accordance with the gastrointestinal tract environment calculated temperature. Alternatively, the mechanism can be controlled by the operator based on the displayed temperature.

It will be appreciated by persons skilled in the art that the present invention is not limited to what has been particularly shown and described hereinabove. Rather the scope of the present invention is defined only by the claims which follows.

What is claimed is:

1. A method for sensing the temperature of an environment comprising the steps of:
   introducing into the environment an image sensor having an image sensing module;
   sensing the dark current noise of the image sensing module;
   calculating the temperature of the image sensor from the sensed dark current noise; and
   calculating the temperature of the environment from the calculated image sensor temperature.

2. A method according to claim 1 further comprising the step of displaying the calculated environment temperature.

3. A method according to claim 1 further comprising the step of amplifying the sensed dark current noise prior to the step of calculating the temperature of the image sensor.

4. A method according to claim 3 wherein the sensed dark current noise is amplified by an integrating unit that is in communication with the image sensor.

5. A method according to claim 1 wherein the step of sensing the dark current noise of the image sensor is performed by an integrating unit that is in communication with the image sensor.

6. A method according to claim 5 wherein any one of the steps subsequent to the step of sensing the dark current noise of the image sensor is performed by a separate unit that is in communication with the integrating unit.

7. A method according to claim 6 wherein the separate unit is located outside of the environment.

8. A method according to claim 5 wherein the integrating unit is located outside of the environment.

9. A method according to claim 1 wherein the steps of calculating the temperature of the image sensor and calculating the temperature of the environment are performed by an integrating unit that is in communication with the image sensor.

10. A method according to claim 1 wherein the image sensor is exposed to intermittent illuminated and dark periods.

11. A method according to claim 10 wherein the step of sensing the dark current noise of the image sensor is performed during one or more dark periods.

12. A method according to claim 1 wherein the image sensor is a video camera.

13. A method according to claim 1 wherein the environment is a body cavity.

14. The method according to claim 1, comprising obtaining visual data.

15. A system for sensing the temperature of an environment comprising an image sensor in communication with an integrating unit,
    said image sensor being introduced into an environment; and
    said integrating unit receiving dark current noise from the image sensor, calculating the temperature of the image sensor, and calculating the temperature of the environment.

16. A system according to claim 15 wherein the integrating unit amplifies the received dark current noise prior to calculating the temperature of the image sensor, and calculating the temperature of the environment.

17. A system according to claim 16 wherein one or more of the steps of amplifying the received dark current noise, calculating the temperature of the image sensor and calculating the temperature of the environment are performed by a separate unit that is in communication with the integrating unit.

18. A system according to claim 17 wherein the separate unit is located outside of the environment.

19. A system according to claim 15 wherein one or both of calculating the temperature of the image sensor and calculating the temperature of the environment are performed by a separate unit that is in communication with the integrating unit.

20. A system according to claim 19 wherein the separate unit is located outside of the environment.

21. A system according to claim 15 wherein the integrating unit further displays the calculated environment temperature.

22. A system according to claim 21 wherein displaying the calculated environment temperature is performed by a separate unit that is in communication with the integrating unit.

23. A system according to claim 22 wherein the separate unit is located outside of the environment.

24. A system according to claim 15 wherein the integrating unit is located outside of the environment.

25. A system according to claim 15 wherein the image sensor is exposed to intermittent illuminated and dark periods.

26. A system according to claim 25 further comprising a switch which is in communication with an illumination indicator for receiving indication of illumination, said switch enabling communication between the image sensor and integrating unit only during one or more dark periods.

27. A system according to claim 26 wherein the switch is capable of accepting signals from an external operator.

28. A system according to claim 15 further comprising a switch which controls illumination elements for exposing the image sensor to intermittent illuminated and dark periods, said switch enabling communication between the image sensor and integrating unit only during one or more dark periods.

29. A system according to claim 28 wherein the switch is capable of accepting signals from an external operator.

30. A system according to claim 15 wherein the integrating unit is in communication with functional units for operating said functional units in accordance with a predetermined temperature.

31. A medical device comprising the system according to claim 30.

32. A medical device according to claim 31 in which the functional units are units that enable the collection of samples from the environment.

33. A system according to claim 15 wherein the image sensor is a video camera.

34. A system according to claim 15 wherein the environment is a body cavity.

35. A medical device comprising the system according to claim 15.

36. A medical device according to claim 35 wherein the device is a swallowable autonomous endoscope.

37. The system according to claim 15, wherein said image sensor is capable of obtaining visual data.

* * * * *